United States Patent [19]

Prusmack

[11] Patent Number: 4,470,409
[45] Date of Patent: Sep. 11, 1984

[54] MEDICAL DEVICE AND METHOD FOR REDUCING DISLOCATED MANDIBLE

[76] Inventor: John P. Prusmack, 11339 Manderson St., Omaha, Nebr. 68164

[21] Appl. No.: 481,796

[22] Filed: Apr. 4, 1983

[51] Int. Cl.³ .............................................. A61F 5/56
[52] U.S. Cl. .................................... 128/136; 128/12; 433/140
[58] Field of Search .................. 433/140; 128/12, 136

[56] References Cited

U.S. PATENT DOCUMENTS 2,570,459 10/1951 Kreider ............................... 433/140
4,179,815 12/1979 Hoffman ............................ 433/140

Primary Examiner—Robert Peshock
Attorney, Agent, or Firm—George R. Nimmer

[57] ABSTRACT

Orally inserted medical device includes a pair of laterally separated upright barriers downwardly abuttably restable along the two lower rows of dental molars supported by the parallel alveolar ridges of the mandible. The physician inserts two index fingers or thumbs into and thus protected by the orally positioned medical device ancillary to manually reducing dislocated mandible. The device barrier components adequately resist uprightly extending dental forces and include semi-hard material at the teeth exposed surfaces, and the device is so constructed as to permit ready accurate insertion into, procedural use within, and removal from, the patient's oral cavity.

12 Claims, 10 Drawing Figures

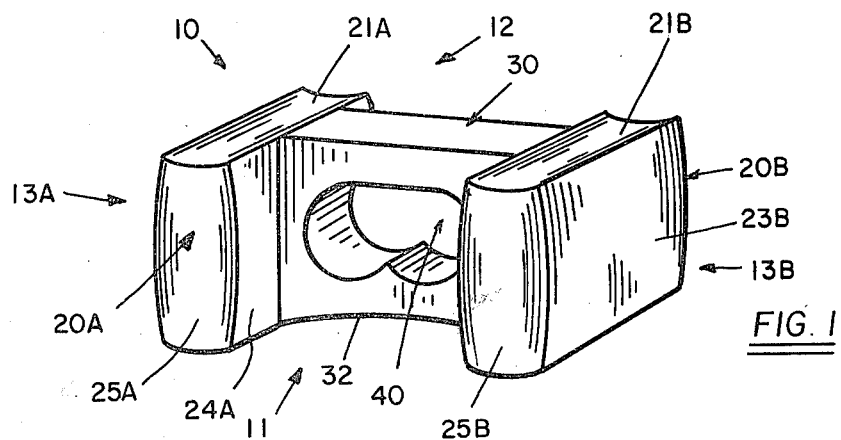
FIG. 1
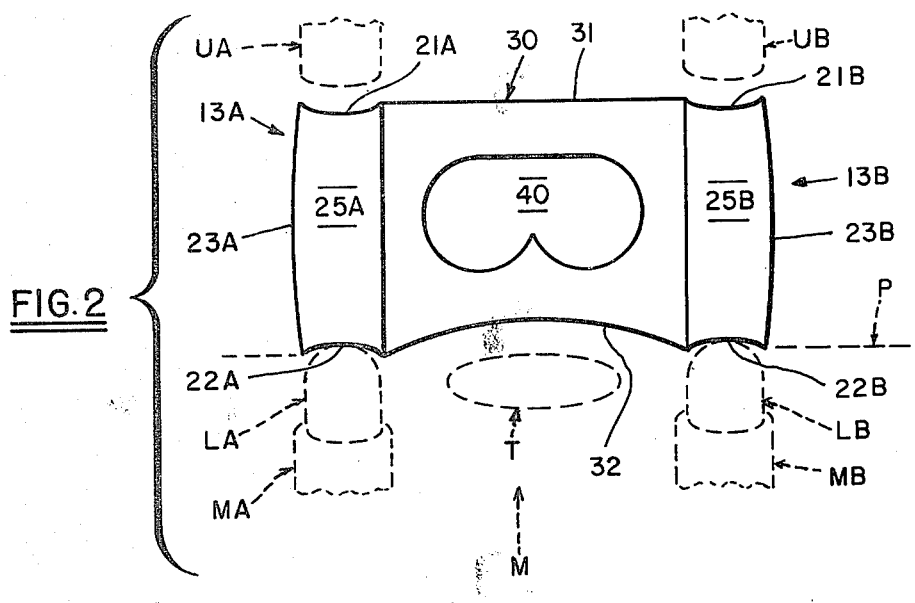
FIG. 2
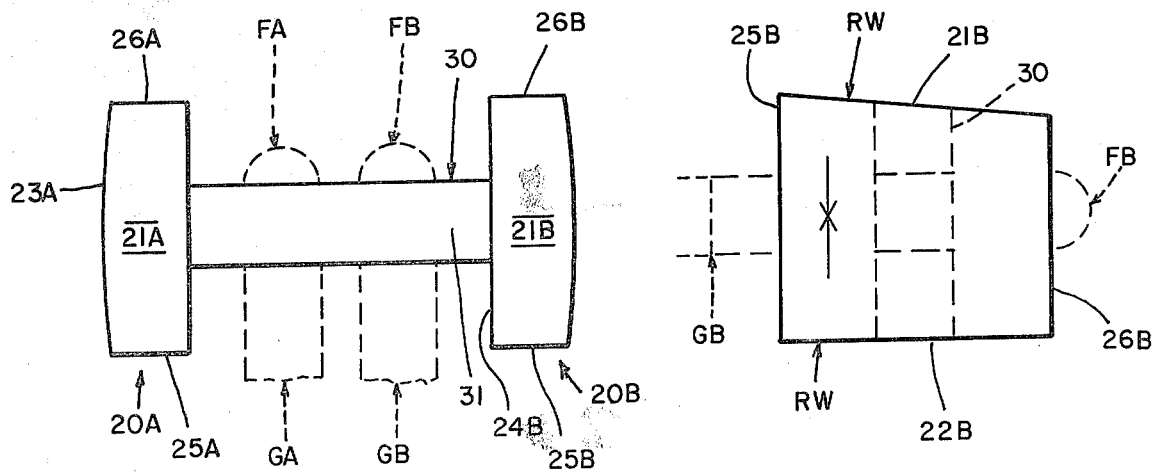
FIG. 3
FIG. 4

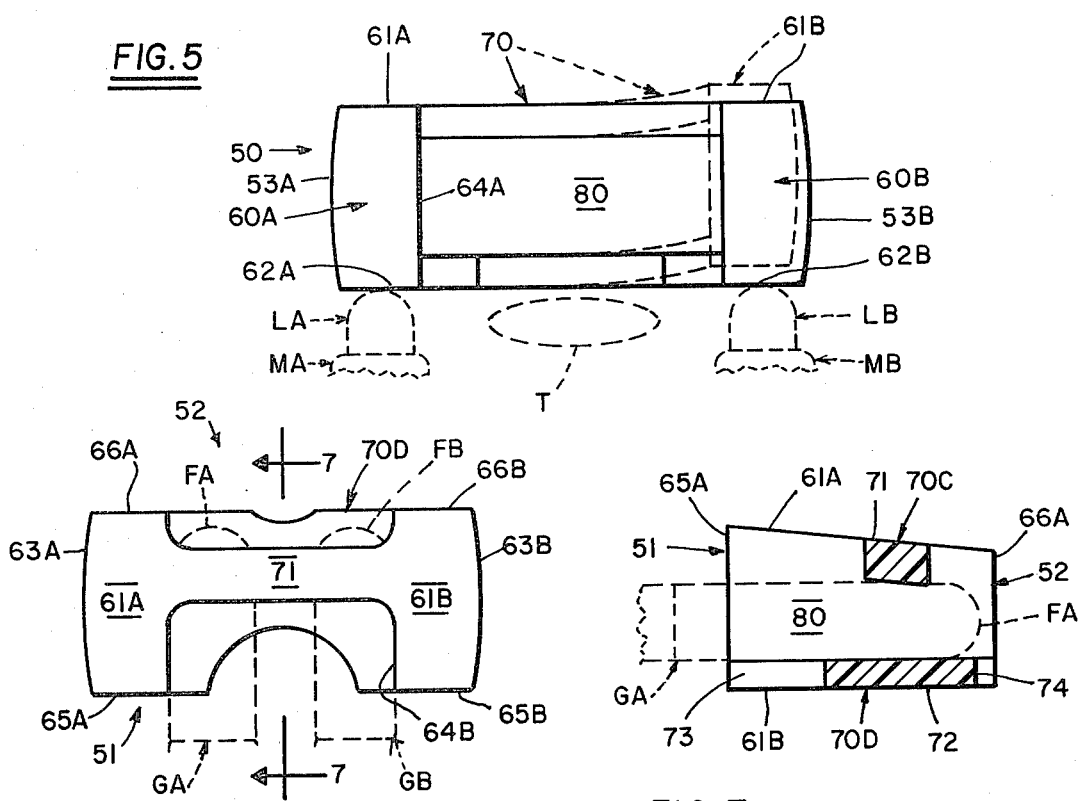
FIG. 5
FIG. 6
FIG. 7
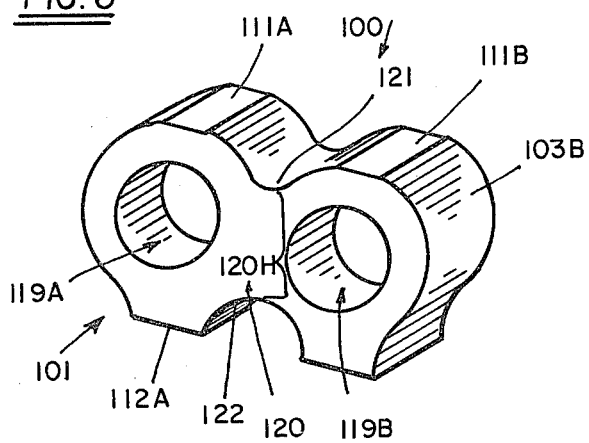
FIG. 8
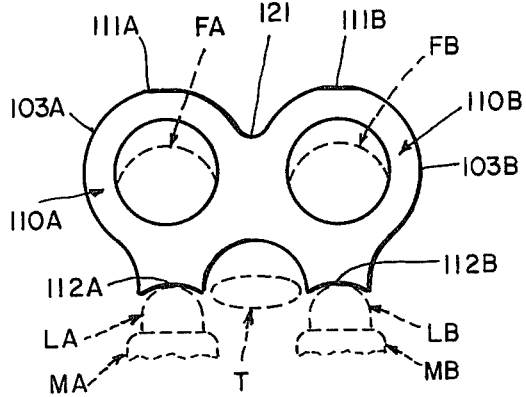
FIG. 9
| RESTING DEVICE BARRIERS AGAINST LOWER MOLARS | → | PRESSING BARRIERS DOWNWARDLY WITH PROTECTED DIGITS | → | MANIPULATING MANDIBLE |
FIG. 10

MEDICAL DEVICE AND METHOD FOR REDUCING DISLOCATED MANDIBLE

BACKGROUND

The anatomical lower jawbone i.e. mandible, is a generally U-shaped bone carrying the lower dental teeth and having its two laterally separated head-ends fitting into the contoured lowerend of the two laterally separated temporal bones. Because of the relatively low ligamental strength between the mandible head-ends and the temporal bones, trauma caused jawbone dislocation from the temporal bones is commonly encountered by attending physicians. The usual medical procedure for treating jawbone dislocation is commonly termed "reducing the mandible" and necessitates skillful manual applications of downward, rearward, and finally upward manual forces to the patient's lower jawbone. Sufficient magnitudes of manual forces in said appropriate directions oftentimes require the physician to insert his thumbs or index fingers within the path of the patient's dental bite; thus, because of patient involuntary muscular reflexes, the medical procedure of "reducing the mandible" is sometimes accompanied by unintentional teeth injury to the attending physician's digits.

OBJECT OF THE INVENTION

It is the general object of the present invention to provide a medical device and improved medical procedure for use in "reducing the mandible" wherein the physician might insert his manual digits protectively within the patient's oral cavity without the danger of being inflicted with teeth injury and wherein the device does not subject the patient to undue discomfort during the procedural use of the device.

SUMMARY OF THE INVENTION

With the above general objective in view, and together with other and ancillary objectives which will become more apparent as this description proceeds, the medical device generally comprises a pair of longitudinally extending and laterally separated upright barriers, each barrier having a generally horizontal bottom-surface adapted to abuttably rest downwardly against molars carried by the mandible laterally separated alveolar ridges, each barrier having a top-surface overlying the bottom-surface and adapted to underlie the upper teeth, said barriers being compressively structurally resistive to uprightly extending dental forces and including semi-hard material at the teeth facing surfaces, each barrier including an upright outer-surface and located at a side-end terminus for the device, the presence of laterally extending bridging means for preferably maintaining lateral spacing of the two barrier components, and longitudinally extending manual digits opening means commencing at the device frontal-side and flanked by the device side-ends terminii whereby both digits of the physician might be simultaneously protectively inserted into the medical device ancillary to an improved procedure for "reducing the madible".

BRIEF DESCRIPTION OF THE DRAWINGS

In the drawing, wherein like characters refer to like parts in the several views, and in which:

FIG. 1 is a perspective view of a representative first embodiment of a medical device for reducing dislocated mandible;

FIG. 2 is a frontal elevational view of the first embodiment, phantom lines indicating typical spatial relationships to the patient's anatomical alveolar ridges, lower molars, tongue, and upper molars;

FIG. 3 is a top plan view of the first embodiment, phantom lines indicating insertion of the physician's manual digits into the device ancillary to mandible reduction procedure therewith;

FIG. 4 is a right side elevational view of the first embodiment;

FIG. 5 is a frontal elevational view of a second embodiment of a medical device for reducing dislocated mandible, additional phantom lines indicating the flexible nature of this embodiment;

FIG. 6 is a top plan view of the second embodiment;

FIG. 7 is a sectional elevational view taken along the longitudinally extending section line 7—7 of FIG. 6;

FIG. 8 is a perspective view of a third embodiment of a medical device for reducing dislocated mandible;

FIG. 9 is a frontal elevational view of the third embodiment, phantom lines indicating spatial relationships to the patient's anatomy and to the physician's manual digits; and FIG. 10 is a schematic flow diagram indicating the novel method for reducing dislocated mandible.

DETAILED DESCRIPTION OF THE DRAWINGS

Environmental patient anatomy for the medical device is indicated in frontal elevational FIGS. 2, 5, and 7, and includes: the U-shaped mandible bone "M" having two laterally separated alveolar ridges "MA" and "MB", lower molars rows "LA" and "LB" carried by said respective ridges "MA" and "MB", tongue "T", and laterally separated upper molar rows "UA" and "UB" directly overlying respective lower rows "LA" and "LB". Alveolar ridges "MA" and "MB", and the molar rows ("LA", "LB", "UA", and "UB"), respectively extend in longitudinal length i.e. perpendicular to the plane of frontal views 2, 5, and 7.

In the general sense, and as represented by embodiment 10 of FIGS. 1–4, the medical device for reducing dislocated mandible basically comprises: a pair of longitudinally extending (25–26) and laterally separated (24A–24B) upright barriers (20A, 20B) having bottom-surfaces (22A, 22B) adapted to abuttably rest upon the lower molars ("LA", "LB") and having top-surfaces (21A, 21B) for underlying upper molars ("UA", "UB"); laterally extending (24A-24B) bridging means attaching the two barriers (20A, 20B) and including a lower-surface (32) opposite the tongue "T" and an upper-surface (31) deeply below the patient's palate; and longitudinally extending manual digits ("FA", "FB") opening means (40) commencing at the device lateral front-end (11) and perhaps extending to the device lateral rear-end (12), and the opening means (40) being flanked by the device longitudinal side-ends terminii (13A, 13B).

Specifically for embodiment 10, each of the twin barriers 20 includes: an upright frontal-surface(25A, 25B) which when in oral position is seen by a physician; an upright rearward-surface (26A, 26B) which is oral position is nearer the manidble head-end than are said frontal-surfaces; a generally horizontal and preferably laterally concave bottom-surface (22A, 22B); a generally horizontal and preferably laterally concave top-surface (21A, 21B); an inner-surface (24A, 24B); and an outer-surface (23A, 23B). The two upright outer-surfaces (23A, 23B) provide the medical device longitudinal side-ends terminii (13A, 13B") respectively flanked by the anatomical cheeks. The two frontal-surfaces (25A, 25B), together with the front-side of bridge 30 provides the device front-end 11; and the two rearward-surfaces (26A, 26B), together with the rear-side of bridge 30 provides the device rear-end 12.

So as to provide an operationally reliable medical device, and one that is sufficiently sturdy to protect the physician's manual digits ("FA", "FB") from inadvertent patient biting and to permit repetitve use with numerous successive patients, certain structural material parameters are necessary. As alluded to by the two-heads arrow in FIG. 4, the structural material compressive strength (between barrier top-surface 21 and bottom-surface 22) should exceed 5,000 p.s.i. And the structural material at barrier top-surface (21) and at barrier bottom-surface (22) should be semi-hard and preferably non-metallic. "Semi-hard" is defined to mean structural material having a durometer hardness within the range of: less than about 100 on the Rockwell M scale (so as to prevent damage to the patient's teeth); and greater than 20 (and preferably exceeding 50) on the Rockwell R scale. The entire medical device might be singularly constructed of resinous or other structural material having the aforedescribed compressive and semi-hard parameters. Or, a major portion of the entire device (except at barrier surfaces 21 and 22) might be singularly constructed of any excessively hard material but having the required compressive strength, and with the "semi-hard" barrier surfaces being as separate adhered laminae.

In representative embodiment 10, the opening means (40) for insertion of the physician+s hands digits is shown entirely confined to the bridging member (30) i.e. flanked by barrier inner-surfaces 24A and 24B. The tow bottom-surfaces (22A, 22B) are preferably laterally concave and co-elevational to facilitate firm abutment against both lower molar rows ("LA", "LB"), and the bridging member lower-surface (32) is preferably laterally concave so as to ensure against interference with the tongue "T" therebelow. The top-surface 21 of each barrier might slope downwardly and rearwardly whereby (as seen in FIG. 4) rearward-surface 26 is shorter than frontal-surface 25 and thereby facilitating insertion into the patient's oral cavity.

Although having already been alluded to, operational use of medical devices for "reducing the mandible" might be summarized as follows. Commencing with rear-end 12, the patient inserts the device (10, 50, 100, etc.) into the patient's oral cavity and aligns the barrier bottom-surfaces (22, 62, 122, etc.) so as to lie along and abuttably rest upon both lower molar rows ("LA", "LB"). Then, the physician inserts both index fingers ("FA", "FB") into the hands digits opening means (40, 80, 119) whereby the respective middle phalanx ("GA", "GB") are located forwardly of device front-end 11. With fingers "FA"and "FB"thus protected by device 10, and with the physician's thumbs simultaneously emplanted beneath the patient's alveolar ridges ("MA", "MB"), the physician bi-manually urges the mandible "M" serially in the downward, the rearward, and the upward directions to "reduce the manible". By virtue of the "semi-hard" bottom-surfaces(22,62,122) and top-surfaces(21,61,121), and the protection offered to the physician (at 40, 80, 119), no damage results to or from any downward movement of the patient's teeth during the novel procedure for reducing accidentally dislocated mandible.

Second embodiment 50 of FIGS. 5-7 differs from embodiment 10 of FIGS. 1-4 primarily at the bridging member. Bridging member 70 comprises a pair of vertically separated horizontal panels 70C and 70D connecting the laterally separated barriers 60A and 60B, said vertical spacing between panels 70C and 70D providing a hands digits opening means 80 extending laterally from the barriers' inner-surfaces 64A and 64B. Inasmuch as the aggregate height of the tow panels 70C and 70D is less than the overall height of either barrier between top-surface (61A, 61B) and bottom-surface (62A, 62B), and considering the resinous structural material employed for panels 70C and 70D, embodiment 50 is manually flexible as indicated in FIG. 5 phantom line. Such manual flexibility permits the physician to temporarily decrease the lateral distance between the side-ends terminii(53A, 53B) to facilitate insertion of of the medical device into the patient's oral cavity. Bottom-panel 70D herein includes frontal-recess 73 and rear-recess 74 to minimize interference with the tongue "T". Other parts of embodiment 50, analagous to like parts of embodiment 10, include: front-end 51; rear-end 52; barrier outer-surfaces (63A, 63B), frontal-surfaces (65A, 65B), and rearward-surfaces(66A, 66B); bridging means upper-surface 71 along top-panel 70C (herein coelevational with top-surfaces 61A, 61B); and bridging means lower-surface 72 along bottom-panel 70D(herein co-elevational with bottom-surfaces 62A, 62B).

Third embodiment 100 of FIGS. 8 and 9 differs from the first and second embodiments primarily in that the hands digits opening means comprises two laterally separated bores 119A and 119B extending longitudinally through the respective barriers (110A, 110B) rather than through the bridging means (120). Analagously as with the first and second embodiments, each barrier has a top-surface (111A, 111B), a bottom-surface (112A, 112B), and an outer-surface together defining the device side-ends terminii(103A, 103B). Also analagously with first bridging embodiment 30, third bridging embodiment 120 includes a laterally extending concave lower-surface 122. Differing from bridge embodiment 30, bridge 120 has a deeply recessed upper-surface 121 whereby the resultant constricted central-height 120H provides for device 110 the manual flexibility akin to that shown in FIG. 4 phantom line.

Drawing FIG. 10 is a schematic diagram alluding to the herebefore described method for reducing dislocated mandible with the medical devices. In FIG. 10, the term "Digits" is used in the general sense because a physician might insert the two thumbs (or perhaps other manual digits), rather than the two index fingers ("FA", "FB") into the device opening (40, 80, 119, etc.).

From the foregoing, the construction and operation of the medical device for reducing dislocated mandible will be readily understood and further explanation is believed to be unnecessary. However, since numerous modifications and changes will readily occur to those skilled in the medical arts, it is not desired to limit the invention to the exact constructions shown and described, and accordingly, further modifications and equivalents may be resorted to, as encompassed by the scope of the appended claims.

I claim:

1. Medical device for use in reducing accidentally dislocated mandible, said device being removably insertable by the attending physician upon the patient's two longitudinally extending and laterally separated rows of lower molars, said device having a laterally extending frontal-end and a laterally extending rearward-end, and two longitudinally extending and laterally separated side-end terminii, and comprising:

A. a pair of longitudinally extending and laterally separated upright barriers, each barrier having a longitudinally extending generally horizontal bottom-surface adapted to abuttably rest downwardly against the two laterally separated rows of lower molars, each barrier having a longitudinally extending generally horizontal top-surface overlying said bottom-surface and adapted to underlie the two laterally separated longitudinal rows of upper molars, each barrier including an upright frontal-surface at the device frontal-end and an upright rearward-surface at the device rearward-end, each barrier including an upright outer-surface whereby the two outer-surfaces define said device side-ends terminii, each barrier between top-surface and bottom-surface having a columnar compressive strength exceeding about 5,000 psi, and each barrier along the top-surface and bottom-surface being provided of a semi-hard structural material;

B. laterally extending bridging means attaching the two upright barriers, said bridging means including a laterally extending upper-surface adapted to deeply underlie the patient's palate and also a laterally extending lower-surface adapted to overlie the patient's tongue; and C. longitudinally extending hands digits opening means commencing at the device frontal-end whereby the physician might insert a finger or thumb digit from each hand into the device for pressing the device downwardly against the mandible-supported two rows of lower molars ancillary to the medical procedure of reducing accidentally dislocated mandible.

2. The medical device of claim 1 wherein the two bottom-surfaces are substantially co-elevational and at an elevation below the bridging means lower-surface.

3. The medical device of claim 2 wherein the top-surface of each barrier slopes downwardly and rearwardly whereby the rearward-surface of each barrier is shorter than the frontal-surface thereof and thereby facilitating insertion of the medical device into the patient's oral cavity.

4. The medical device of claim 1 wherein the hands digits opening means comprises a pair of longitudinally extending and laterally separated bores.

5. The medical device of claim 4 wherein each barrier commencing at the frontal-surface thereof is provided with a said bore.

6. The medical device of claim 1 wherein the hands digits opening means in confined in lateral position between the two up-right barriers.

7. The medical device of claim 1 wherein the aggregate height of the bridging means structural material is less than the overall height of either barrier between top-surface and bottom-surface whereby the device might flex at the bridging means for easier insertion into the patient's oral cavity.

8. The medical device of claim 3 wherein the bridging means has a concave lower-surface so as to be spatially separated from the patient's tongue, and said lower-surface being located at higher elevation than the co-elevational bottom-surfaces.

9. The medical device of claim 8 wherein each barrier along top-surface and bottom-surface is of non-metallic structural material having a durometer hardness within the range of: less than about 100 on the Rockwell M scale, and greater than about 20 on the Rockwell R scale.

10. The medical device of claim 1 wherein each barrier along top-surface and bottom-surface is of non-metallic structural material having a durometer hardness within the range of: less than about 100 on the Rockwell M scale, and greater than about 20 on the Rockwell R scale.

11. The medical device of claim 10 wherein the major portion of both barriers and bridging means are singularly constructed of the same structural material.

12. Method for reducing accidentally dislocated mandible, said method comprising the following steps performed by the operator upon the patient:

A. inserting into the patient's oral cavity above the tongue and two longitudinally extending rows of lower molars a medical device comprising a pair of longitudinally extending and laterally separated upright barriers, each barrier having a longitudinally extending generally horizontal bottom-surface adapted to abuttably downwardly rest against the two laterally separated rows of mandible supported lower molars, each barrier having a longitudinally extending generally horizontal top-surface overlying said bottom-surface and adapted to underlie the two laterally separated rows of upper molars, said top-surfaces and bottom-surfaces being provided of semi-hard structural material, and said device including longitudinally extending hands digits opening means;

B. ensuring that the bottom-surfaces of the two barriers lie longitudinally along and abuttably rest downwardly upon the two lower rows of molars;

C. longitudinally inserting a digit from both of the operator's hands into said device digits opening means whereby the operator's digits are protected by the device from the patient's dental teeth; and D. simultaneously pressing downwardly with both protected digits to cause the device bottom-surfaces to press downwardly against the two lower rows of molars carried by the patient's mandible and accompanied by urging the patient's mandible in the rearward direction toward the lower-ends of the patient's temporal bones.

* * * * *